US006953580B2

(12) United States Patent
Tanaka et al.

(10) Patent No.: US 6,953,580 B2
(45) Date of Patent: Oct. 11, 2005

(54) COMPOSITION HAVING PHYSIOLOGICAL ACTIVITY AND PRODUCTION METHOD THEREOF

(75) Inventors: Hozumi Tanaka, Kobe (JP); Ken Hibino, Ibaraki (JP); Yasuyo Hijikata, Ibaraki (JP)

(73) Assignee: Nitto Denko Corporation, Ibaraki (JP)

( * ) Notice: Subject to any disclaimer, the term of this patent is extended or adjusted under 35 U.S.C. 154(b) by 0 days.

(21) Appl. No.: 10/202,565

(22) Filed: Jul. 24, 2002

(65) Prior Publication Data

US 2003/0021857 A1 Jan. 30, 2003

(30) Foreign Application Priority Data

Jul. 24, 2001 (JP) ........................................ 2001-223334

(51) Int. Cl.$^7$ ............................................. A61K 35/78
(52) U.S. Cl. .................. 424/195.15; 424/728; 424/725
(58) Field of Search ............................ 424/195.15, 728, 424/725

(56) References Cited

U.S. PATENT DOCUMENTS 5,840,308 A * 11/1998 Jassim et al.

FOREIGN PATENT DOCUMENTS

| JP | 02-36124 A | * | 2/1990 |
| JP | 09-136839 | | 5/1997 |
| WO | WO 99/56567 | * | 11/1999 |

OTHER PUBLICATIONS

Ganoderma Internet article (www.ibiblio.org/hermed/archives/Best/1994/ganoderma.html) 1994.*

* cited by examiner

*Primary Examiner*—Susan D. Coe
(74) *Attorney, Agent, or Firm*—Leydig, Voit & Mayer, Ltd.

(57) ABSTRACT

The present invention provides a composition containing an extract from *Wisteria floribunda, Myristica fragrans, Punica granatum, Trapa bispinosa* or a derivative thereof, *Coix lachiryma-jobi, Elfvingia applanata* and *Ganoderma lucidum* or a derivative thereof (optionally further containing *Panax ginseng* or *Panax japonicus*), which has a superior antiviral activity, a superior peripheral blood flow-improving activity and a superior hair growth-stimulating activity, and a production method thereof.

17 Claims, 1 Drawing Sheet

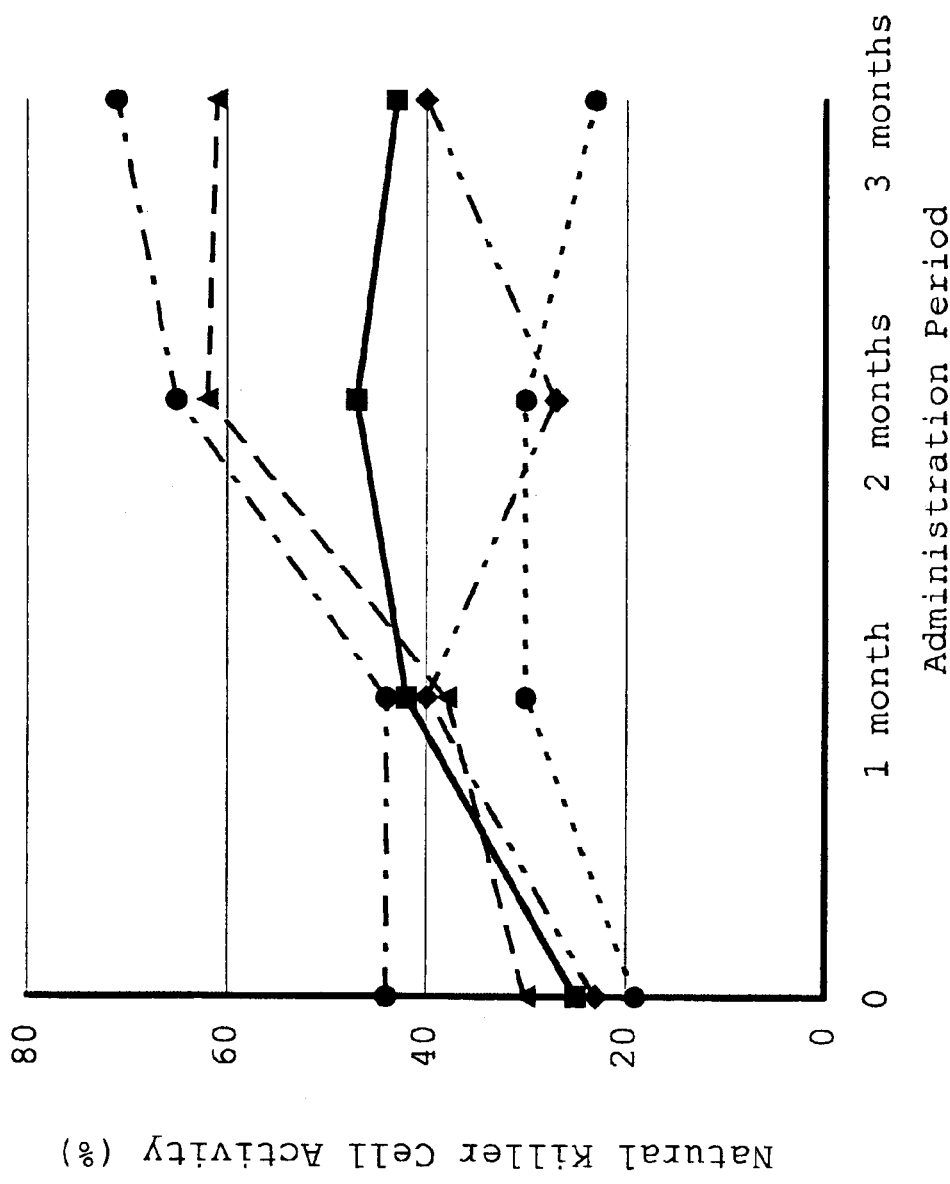
Fig. 1 Effect of Formula B on Natural Killer Cell Activity

COMPOSITION HAVING PHYSIOLOGICAL ACTIVITY AND PRODUCTION METHOD THEREOF

TECHNICAL FIELD

The present invention relates to a novel physiologically active composition. More particularly, the present invention relates to a novel composition having a useful physiological activity as an agent for treating viral infectious diseases, a peripheral blood flow-improving agent or a hair growth stimulant, and a production method thereof.

BACKGROUND ART

As a pharmaceutical agent effective for the treatment or prophylaxis of bacterial infections, various superior pharmaceutical agents have been developed. However, the number of pharmaceutical agents effective for the treatment or prophylaxis of viral infectious diseases is relatively small and most of them show strong side effects.

For example, herpes simplex virus is known to be widespread among adults, mainly infects lips, oral mucosa, cornea and genitalia and causes latent infection in the nervous tissues. In addition, new herpes virus infectious diseases have been found. As a conventional anti-herpes simplex virus agent, acyclovir, which is a nucleic acid derivative, and the like have been clinically used because they are effective pharmaceutical agents. Acyclovir, nevertheless, causes problems in the treatment because the virus easily becomes resistant and shows strong side effects.

In addition, varicella-zoster virus (herpes zoster virus) is initially infected as, what is called, varicella in infancy, and latently infected thereafter. After maturity, herpes zoster is developed when the cellular immunity is degraded. Again, acyclovir is used as an antiviral agent, but its effect is considered to be weaker than that against herpes simplex virus. There are only a few antiviral agents effective against rubella virus or hepatitis B virus.

As a peripheral blood flow-improving agent, a representative pharmaceutical product in the conventional art is prostaglandin $E_1$. However, prostaglandin $E_1$ is problematic in that it shows side effects such as angialgia and the like. It is not available without a physician's prescription, and a superior oral pharmaceutical agent that improves peripheral blood flow upon habitual use thereof for preventive purposes has not been provided as yet.

As regards a hair growth stimulant, those provided by conventional techniques are mostly external medicine type quasi-drugs to be directly applied to the head irrespective of the dosage form. As an oral administration type hair growth stimulant, there are galenicals for folkloric use, such as *Polygonum multiflorum, Cuscutae Semen, Psoralea corylifolia* and the like, but their effect is generally extremely weak.

It is therefore an object of the present invention to provide a novel composition having a physiological activity useful as an agent for treating viral infectious diseases, a peripheral blood flow-improving agent or a hair growth stimulant, and a production method thereof.

DISCLOSURE OF THE INVENTION

According to the present invention, it has been found that a composition containing an extract from *Wisteria floribunda, Myristica fragrans, Punica granatum, Trapa bispinosa* or a derivative thereof, which may be *T. natans, T. bicornus* or *T. japonica, Coix lachryma-jobi, Elfvingia applanata* and *Ganoderma lucidum* or a derivative thereof (e.g., *G. japonicum*), and such composition further containing an extract from *Panax ginseng* or *Panax japonicus* have a superior antiviral activity, a superior peripheral blood flow-improving activity and a superior hair growth-stimulating activity.

[1] A composition containing an extract from *Wisteria floribunda, Myristica fragrans, Punica granatum, Trapa bispinosa* or a derivative thereof, *Coix lachryma-jobi, Elfvingia applanata* and *Ganoderma lucidum* or a derivative thereof.

[2] The composition of the above-mentioned [1], further containing an extract from *Panax ginseng* or *Panax japonicus*.

[3] The composition of the above-mentioned [1] or [2], wherein the extract is a hot water extract.

[4] The composition of the above-mentioned [1], which contains an extract obtained from 0.5 part by weight-5 parts by weight of *Myristica fragrans*, 0.5 part by weight-5 parts by weight of *Punica granatum*, 0.5 part by weight-5 parts by weight of *Trapa bispinosa* or a derivative thereof, 0.5 part by weight-5 parts by weight of *Elfvingia applanata*, 0.5 part by weight-5 parts by weight of *Coix lachryma-jobi*, and 0.5 part by weight-5 parts by weight of *Ganoderma lucidum* or a derivative thereof, per 1 part by weight of *Wisteria floribunda*.

[5] The composition of the above-mentioned [4], which contains an extract obtained from 1 part by weight of *Myristica fragrans*, 1 part by weight of *Punica granatum*, 1 part by weight of *Trapa bispinosa* or a derivative thereof, 1 part by weight of *Elfvingia applanata*, 2 parts by weight of *Coix lachryma-jobi* and 2 parts by weight-3 parts by weight of *Ganoderma lucidum* or a derivative thereof, per 1 part by weight of *Wisteria floribunda*.

[6] The composition of the above-mentioned [5], which contains an extract obtained from 1 part by weight of *Myristica fragrans*, 1 part by weight of *Punica granatum*, 1 part by weight of *Trapa bispinosa* or a derivative thereof, 1 part by weight of *Elfvingia applanata*, 2 parts by weight of *Coix lachryma-jobi* and 2 parts by weight of *Ganoderma lucidum* or a derivative thereof, per 1 part by weight of *Wisteria floribunda*.

[7] The composition of the above-mentioned [2], which contains an extract obtained from 0.5 part by weight-5 parts by weight of *Myristica fragrans*, 0.5 part by weight-5 parts by weight of *Punica granatum*, 0.5 part by weight-5 parts by weight of *Trapa bispinosa* or a derivative thereof, 0.5 part by weight-5 parts by weight of *Elfvingia applanata*, 0.5 part by weight-5 parts by weight of *Coix lachryma-jobi*, 0.5 part by weight-5 parts by weight of *Ganoderma lucidum* or a derivative thereof, and 0.5 part by weight-5 parts by weight of *Panax ginseng* or *Panax japonicus*, per 1 part by weight of *Wisteria floribunda*.

[8] The composition of the above-mentioned [7], which contains an extract obtained from 1 part by weight of *Myristica fragrans*, 1 part by weight of *Punica granatum*, 1 part by weight of *Trapa bispinosa* or a derivative thereof, 1 part by weight of *Elfvingia applanata*, 2 parts by weight of *Coix lachryma-jobi*, 2 parts by weight-3 parts by weight of *Ganoderma lucidum* or a derivative thereof, and 0.5 part by weight-3 parts by weight of *Panax ginseng* or *Panax japonicus*, per 1 part by weight of *Wisteria floribunda*.

[9] The composition of the above-mentioned [8], which contains an extract obtained from 1 part by weight of

*Myristica fragrans,* 1 part by weight of *Punica granatum,* 1 part by weight of *Trapa bispinosa* or a derivative thereof, 1 part by weight of *Elfvingia applanata,* 2 parts by weight of *Coix lachryma-jobi,* 2 parts by weight of *Ganoderma lucidum* or a derivative thereof, and 2 parts by weight of *Panax ginseng* or *Panax japonicus,* per 1 part by weight of *Wisteria floribunda.*

[10] The composition of any of the above-mentioned [1]–[9], which is used for treating a viral infectious disease.

[11] The composition of the above-mentioned [10], wherein the viral infectious disease is caused by herpes virus, rubella virus or hepatitis B virus.

[12] The composition of the above-mentioned [11], wherein the herpes virus is a herpes simplex virus or a varicella-zoster virus.

[13] The composition of any of the above-mentioned [1]–[9], which is used for improving peripheral blood flow.

[14] The composition of any of the above-mentioned [1]–[9], which is used for stimulating hair growth.

[15] A method for producing a composition having a physiological activity, comprising extracting *Wisteria floribunda, Myristica fragrans, Punica granatum, Trapa bispinosa* or a derivative thereof, *Coix lachryma-jobi, Elfvingia applanata* and *Ganoderma lucidum* or a derivative thereof, with hot water.

[16] The production method of the above-mentioned [15] comprising extracting, with hot water, 0.5 part by weight-5 parts by weight of *Myristica fragrans,* 0.5 part by weight-5 parts by weight of *Punica granatum,* 0.5 part by weight-5 parts by weight of *Trapa bispinosa* or a derivative thereof, 0.5 part by weight-5 parts by weight of *Elfvingia applanata,* 0.5 part by weight-5 parts by weight of *Coix lachryma-jobi,* and 0.5 part by weight-5 parts by weight of *Ganoderma lucidum* or a derivative thereof, per 1 part by weight of *Wisteria floribunda.*

[17] A method for producing a composition having a physiological activity, comprising extracting *Panax ginseng* or *Panax japonicus,* and *Wisteria floribunda, Myristica fragrans, Punica granatum, Trapa bispinosa* or a derivative thereof, *Coix lachryma-jobi, Elfvingia applanata* and *Ganoderma lucidum* or a derivative thereof, with hot water.

[18] The production method of the above-mentioned [17] comprising extracting, with hot water, 0.5 part by weight-5 parts by weight of *Myristica fragrans,* 0.5 part by weight-5 parts by weight of *Punica granatum,* 0.5 part by weight-5 parts by weight of *Trapa bispinosa* or a derivative thereof, 0.5 part by weight-5 parts by weight of *Elfvingia applanata,* 0.5 part by weight-5 parts by weight of *Coix lachryma-jobi,* 0.5 part by weight-5 parts by weight of *Ganoderma lucidum* or a derivative thereof, and 0.5 part by weight-5 parts by weight of *Panax ginseng* or *Panax japonicus,* per 1 part by weight of *Wisteria floribunda.*

[19] The production method of any of the above-mentioned [15] to [18], wherein the hot water extraction is performed at 80° C.–100° C. for not less than 1 hr.

[20] The production method of the above-mentioned [19], wherein the hot water extraction is performed at 90° C.–95° C. for not less than 1 hr.

BRIEF DESCRIPTION OF THE DRAWING

FIG. 1 shows an effect of the composition of the present invention on the activity of natural killer cell.

DETAILED DESCRIPTION OF THE INVENTION

The composition of the present invention contains an extract from *Wisteria floribunda, Myristica fragrans, Punica granatum, Trapa bispinosa* or a derivative thereof which may be *T. natans, T. bicornus* or *T. japonica, Coix lachryma-jobi, Elfvingia applanata* and *Ganoderma lucidum* or a derivative thereof (e.g., *G. japonicum*) as an essential component.

*Wisteria floribunda* is a medium-sized climbing woody vine of a Leguminosae family naturally growing in the mountains in Japan, and its stem is used. It contains isoflavonoid and the like as components and has been conventionally used for the treatment of gastric cancer, and the like. However, there is no report on the superior bioactivity that this galenical has, such as an antiviral activity, a peripheral blood flow-improving activity and a hair growth-stimulating activity.

*Myristica fragrans* is famous as a headache cure and a gastrointestinal drug in the Indian ancient Ayurveda, and has been used for dyspepsia, bellyache, diarrhea and vomiting in the traditional Chinese medicine. However, there is no report on the antiviral activity, peripheral blood flow-improving activity or hair growth-stimulating activity of this galenical.

*Punica granatum* (its dried seed vessel is used) is frequently used for diarrhea. While its antiviral activity is taught in local folkloric medicine, its peripheral blood flow-improving activity or hair growth-stimulating activity has not been reported.

*Trapa bispinosa* and derivatives thereof are plant fruits of a Trapaceae family naturally growing in China, Korea and Japan, contain sterol as a component and are conventionally known to have a fever-lowering effect. However, there is no report on the antiviral activity, peripheral blood flow-improving activity or hair growth-stimulating activity of this galenical.

*Coix lachryma-jobi* belongs to a Gramineae family and its matured seed without a seed coat is used. It contains starch, protein, fats, as well as an antitumor component, and is conventionally known to have an antitumor effect. It is also used as a special remedy for wart. However, there is no report on the antiviral activity, peripheral blood flow-improving activity or hair growth-stimulating activity of this galenical.

*Elfvingia applanata* belongs to a Polyporaceae family in Basidiomycetes, contains polysaccharide and steroids as components, and is conventionally known to have a carcinostatic action.

*Ganoderma lucidum* and derivatives thereof belong to a Polyporaceae family in Basidiomycetes, contain polysaccharide and triterpenoids as components, and are conventionally known to have an anticancer activity.

Polysaccharides obtained from basidiomycetes of a Polyporaceae family, such as *Elfvingia applanata, Ganoderma lucidum* and derivatives thereof and the like, have been confirmed to have a strong antitumor activity, but their antiviral activity, peripheral blood flow-improving activity or hair growth-stimulating activity has not been reported.

Each extracted component of the above-mentioned *Wisteria floribunda, Myristica fragrans, Punica granatum, Trapa bispinosa* and derivatives thereof, *Coix lachryma-jobi, Elfvingia applanata* and *Ganoderma lucidum* and derivatives thereof does not show a particularly remarkable antiviral activity, peripheral blood flow-improving activity or hair growth-stimulating activity on its own. The composition of the present invention contains all the extracted components of *Wisteria floribunda, Myristica fragrans, Punica granatum, Trapa bispinosa* or a derivative thereof, *Coix lachryma-jobi, Elfvingia applanata* and *Ganoderma lucidum* or a derivative thereof as essential components, whereby a superior physiological activity, such as a remarkable antiviral activity, a peripheral blood flow-improving activity and a hair growth-stimulating activity, is provided.

The composition of the present invention preferably contains, in addition to the above-mentioned *Wisteria floribunda, Myristica fragrans, Punica granatum, Trapa bispinosa, Coix lachryma-jobi, Elfvingia applanata* and *Ganoderma lucidum*, an extract from *Panax ginseng* or *Panax japonicus*. By the addition of an extract from *Panax ginseng* or *Panax japonicus*, the composition of the present invention shows improved activities in the above-mentioned antiviral activity, peripheral blood flow-improving activity and hair growth-stimulating activity.

*Panax ginseng* is a plant of an Araliaceae family, which grows naturally or is cultivated in the Korean peninsula, China and Japan. It contains saponin as a component, and is conventionally known to have an anti-fatigue, hypoglycemic, stomachic, sedative actions and the like. However, there is no report on the antiviral activity, peripheral blood flow-improving activity or hair growth-stimulating activity of this galenical.

*Panax ginseng* in the present invention may be naturally occurring, cultivated or a tissue culture product, whose derivation is not particularly limited. *Panax ginseng* in the present invention is what is called *Panax ginseng*, and *Panax japonicus* may be used instead of the *Panax ginseng*.

The composition of the present invention contains an extract from *Wisteria floribunda, Myristica fragrans, Punica granatum, Trapa bispinosa* or a derivative thereof, *Coix lachryma-jobi, Elfvingia applanata* and *Ganoderma lucidum* or a derivative thereof and preferably an extract from *Panax ginseng* or *Panax japonicus*, in addition to such essential components. The extraction method is not particularly limited and the extract may be obtained by conventionally known various extraction methods. Because a composition having the objective high physiological activity (efficacy) can be obtained, an extract obtained by hot water extraction (hot water extract) is preferable.

The above-mentioned extract may be obtained from a mixture containing *Wisteria floribunda, Myristica fragrans, Punica granatum, Trapa bispinosa* or a derivative thereof, *Coix lachryma-jobi, Elfvingia applanata* and *Ganoderma lucidum* or a derivative thereof, or the above-mentioned 7 kinds of herbs may be separately extracted and the obtained extract components may be mixed. When an extract containing an extract from *Panax ginseng* or *Panax japonicus* is desired, it may be obtained from a mixture containing *Panax ginseng* (or *Panax japonicus*), *Wisteria floribunda, Myristica fragrans, Punica granatum, Trapa bispinosa* or a derivative thereof, *Coix lachryma-jobi, Elfvingia applanata* and *Ganoderma lucidum* or a derivative thereof, or the above-mentioned 8 kinds of herbs may be separately extracted and the obtained extract components may be mixed.

The composition of the present invention preferably contains an extract obtained from 0.5 part by weight-5 parts by weight of *Myristica fragrans*, 0.5 part by weight-5 parts by weight of *Punica granatum*, 0.5 part by weight-5 parts by weight of *Trapa bispinosa* or a derivative thereof, 0.5 part by weight-5 parts by weight of *Elfvingia applanata*, 0.5 part by weight-5 parts by weight of *Coix lachryma-jobi*, and 0.5 part by weight-5 parts by weight of *Ganoderma lucidum* or a derivative thereof, relative to 1 part by weight of *Wisteria floribunda*. In addition to the above-mentioned, it preferably further contains an extract from 0.5 part by weight-5 parts by weight of *Panax ginseng* or *Panax japonicus*.

The composition of the present invention preferably contains an extract obtained from 0.7 part by weight-3 parts by weight of *Myristica fragrans*, 0.7 part by weight-3 parts by weight of *Punica granatum*, 0.7 part by weight-3 parts by weight of *Trapa bispinosa* or a derivative thereof, 0.7 part by weight-3 parts by weight of *Elfvingia applanata*, 0.7 part by weight-3 parts by weight of *Coix lachryma-jobi*, and 0.7 part by weight-3 parts by weight of *Ganoderma lucidum* or a derivative thereof, relative to 1 part by weight of *Wisteria floribunda*, and more preferably contains an extract from 0.7 part by weight-3 parts by weight of *Panax ginseng* or *Panax japonicus*.

Moreover, the composition of the present invention is particularly preferably an extract from 1 part by weight of *Myristica fragrans*, 1 part by weight of *Punica granatum*, 1 part by weight of *Trapa bispinosa* or a derivative thereof, 1 part by weight of *Elfvingia applanata*, 2 parts by weight of *Coix lachryma-jobi*, and 2 parts by weight of *Ganoderma lucidum* or a derivative thereof, relative to 1 part by weight of *Wisteria floribunda*. Depending on the conditions, *Ganoderma lucidum* or a derivative thereof may be used in a proportion of 2 parts by weight-10 parts by weight (preferably 2 parts by weight-3 parts by weight) relative to 1 part by weight of *Wisteria floribunda*.

When an extract from *Panax ginseng* or *Panax japonicus* is contained, it is preferably an extract obtained from 1 part by weight of *Myristica fragrans*, 1 part by weight of *Punica granatum*, 1 part by weight of *Trapa bispinosa* or a derivative thereof, 1 part by weight of *Elfvingia applanata*, 2 parts by weight of *Coix lachryma-jobi*, 2 parts by weight-3 parts by weight of *Ganoderma lucidum* or a derivative thereof, and 0.5 part by weight-3 parts by weight of *Panax ginseng* or *Panax japonicus*, relative to 1 part by weight of *Wisteria floribunda*. It is more preferably an extract obtained from 1 part by weight of *Myristica fragrans*, 1 part by weight of *Punica granatum*, 1 part by weight of *Trapa bispinosa* or a derivative thereof, 1 part by weight of *Elfvingia applanata*, 2 parts by weight of *Coix lachryma-jobi*, 2 parts by weight of *Ganoderma lucidum* or a derivative thereof, and 2 parts by weight of *Panax ginseng* or *Panax japonicus*, relative to 1 part by weight of *Wisteria floribunda*. Depending on the conditions, *Ganoderma lucidum* or a derivative thereof may be used in a proportion of 2 parts by weight-10 parts by weight (preferably 2 parts by weight-3 parts by weight), relative to 1 part by weight of *Wisteria floribunda*.

The composition of the present invention is preferably obtained by hot water extraction of *Wisteria floribunda, Myristica fragrans, Punica granatum, Trapa bispinosa* or a derivative thereof, *Coix lachryma-jobi, Elfvingia applanata* and *Ganoderma lucidum* or a derivative thereof, and where necessary, *Panax ginseng* or *Panax japonicus*, in the aforementioned suitable amounts of addition.

The temperature conditions and time conditions for the hot water extraction are not particularly limited, and they may be general conditions for hot water extraction (e.g., general conditions for preparation of decoction; about 30 min to 60 min extraction at the boiling temperature). The temperature is preferably 80° C.–100° C., more preferably 90° C.–95° C., and the time is preferably not less than 1 hr, more preferably not less than 2 hr, particularly preferably not less than 3 hr. The hot water extraction under such temperature conditions and time conditions are preferable in that a highly effective composition can be obtained. The amount of water used for the hot water extraction is not particularly limited, but it is generally 5 parts by weight-20 parts by weight of water, preferably about 10 parts by weight of water, per 1 part by weight of the herbal material.

By concentrating the obtained extract (extract solution), unnecessary volatile components can be removed and a preparation less burdensome on the digestive organs and the like by oral administration of a large amount can be obtained. The extract is preferably concentrated under the atmospheric pressure or under reduced pressure at 50° C.–90° C., more preferably under reduced pressure at 50° C.–60° C., to a solid content concentration to about 20 wt %–40 wt %, preferably about 25 wt %–35 wt %.

Furthermore, by adding an excipient to the obtained concentrate and drying, a stable powder preparation can be obtained. The excipient is not particularly limited as long as it is acceptable as a food or pharmaceutical agent, such as starch (e.g., cornstarch, potatostarch, wheat starch, rice starch), glucose, fructose, sorbitol, mannitol, carboxymethyl cellulose, carboxymethyl cellulose calcium, lactose, sucrose, hydroxypropyl cellulose, magnesium carbonate, magnesium oxide, calcium phosphate and the like. The amount of addition of the excipient is generally about 1 part by weight-20 parts by weight, preferably about 2 parts by weight-10 parts by weight, per 1 part by weight of the concentrate. The drying is preferably conducted at a temperature of 60° C.–70° C.

The composition of the present invention shows a remarkable antiviral activity, a remarkable peripheral blood flow-improving activity and a remarkable hair growth-stimulating activity, and is particularly useful as an agent for treating viral infectious diseases, a peripheral blood flow-improving agent, or a hair growth stimulant. The subject of administration of the agent for treating viral infectious diseases, a peripheral blood flow-improving agent or a hair growth stimulant containing the composition of the present invention is not particularly limited, but it is a mammal such as human, bovine, horse, dog, cat and the like, particularly preferably human.

When the composition of the present invention is used as an agent for treating viral infectious diseases, it is particularly effective against infection with various viruses such as viruses of herpes family (e.g., type 1 and type 2 of herpes simplex viruses, varicella-zoster virus and the like), rubella virus, hepatitis B virus and the like, and is particularly effective against infection with herpes simplex virus.

When the composition of the present invention is used as a peripheral blood flow-improving agent or hair growth stimulant, it is particularly effective in mammals such as human and the like.

The composition of the present invention is obtained from conventionally used galenical materials as a starting material, and the toxicity at an effective dose is extremely low, showing almost no side effects. Thus, the composition can be safely administered to mammals such as human, bovine, horse, dog, cat and the like.

A preferable Formula Example (Formula A) of the composition of the present invention having a physiological activity is as follows.

*Wisteria floribunda, Myristica fragrans, Punica granatum, Trapa bispinosa* or a derivative thereof, *Elfvingia applanata, Coix lachryma-jobi* and *Ganoderma lucidum* or a derivative thereof [the mixing ratio is preferably 1:1:1:1:1:2:2 (weight ratio), but *Ganoderma lucidum* or a derivative thereof may be increased to a 2-fold weight to 3-fold weight] are mixed, and extracted with an about 10-fold weight of hot water (80° C.–100° C.) relative to the total weight of the herbal materials. The extract is concentrated to give starch syrup, to which an about 2-fold weight of a starch powder is added, mixed and kneaded to homogeneity and dried to give a powder. Generally, about 8 g of a preparation is obtained from 12 g–16 g of a herbal material composition.

Another preferable Formula Example (Formula B) of the composition having a physiological activity of the present invention is as follows.

*Wisteria floribunda, Myristica fragrans, Punica granatum, Trapa bispinosa* or a derivative thereof, *Elfvingia applanata, Coix lachryma-jobi, Ganoderma lucidum* or a derivative thereof and *Panax ginseng* (or *Panax japonicus*) [the mixing ratio is preferably 1:1:1:1:1:2:2:2 (weight ratio), but *Ganoderma lucidum* or a derivative thereof may be increased to a 2-fold weight to 3-fold weight] are mixed, and extracted with an about 10-fold weight of hot water (80° C.–100° C.) relative to the total weight of the herbal materials. The extract is concentrated to give starch syrup, to which an about 2-fold weight of a starch powder is added, mixed and kneaded to homogeneity and dried to give a powder. Generally, about 6 g of a preparation is obtained from 12 g–20 g of a galenical starting material composition.

Generally, an extract from *Wisteria floribunda, Myristica fragrans, Punica granatum, Trapa bispinosa* or a derivative thereof, *Coix lachryma-jobi, Elfvingia applanata* and *Ganoderma lucidum* or a derivative thereof, which is the active ingredient of the present invention, or an extract from *Panax ginseng* (or *Panax japonicus*), *Wisteria floribunda, Myristica fragrans, Punica granatum, Trapa bispinosa* or a derivative thereof, *Coix lachryma-jobi, Elfvingia applanata* and *Ganoderma lucidum* or a derivative thereof, is admixed with a pharmaceutically acceptable carrier or additive and used in the form of a pharmaceutical composition suitable for administration. The form of the pharmaceutical composition is not particularly limited, and a preparation in the form of a powder, granule, tablet, pill, capsule, liquid, emulsion, suspension, syrup, troche, suppository, eye drop, injection, aerosol, elixir and the like can be obtained.

The pharmaceutically acceptable carrier or additive is exemplified by an excipient (e.g., starch, glucose, fructose, sorbitol, mannitol, carboxymethyl cellulose, carboxymethyl cellulose calcium, lactose, sucrose, hydroxypropyl cellulose, magnesium carbonate, magnesium oxide, calcium phosphate), a binder (e.g., gum arabic, carboxymethyl cellulose, carboxymethyl cellulose sodium, gelatin, dextrin, hydroxypropyl cellulose, polyvinylpyrrolidone, polyethylene glycol, starch, sucrose), a disintegrant (e.g., carboxymethyl cellulose, carboxymethyl cellulose calcium, starch, hydroxypropyl cellulose), a lubricant (e.g., magnesium silicate, calcium stearate, magnesium stearate, talc), a diluent (e.g., water, brine, vegetable oil such as soybean oil, sesame oil and olive oil), an ointment base (e.g., paraffin, lanolin, white petrolatum), a flavoring agent (e.g., sucrose, simple syrup, peppermint oil, orange oil), a preservatives (e.g., p-oxybenzoic acid esters such as methyl p-oxybenzoate, ethyl p-oxybenzoate and propyl p-oxybenzoate, sodium benzoate), a stabilizer (e.g., ascorbic acid, sodium hydrogen sulfite), an isotonicity agent (e.g., sodium chloride, glycerine, glucose, mannitol) and the like.

The composition of the present invention can be administered orally or parenterally, generally by oral administration.

In the case of oral administration, the general dose (usual dose) is as follows, wherein the dose is appropriately determined to about ¼–3-fold amount of the usual dose depending on the age and sex of individual, symptom, physical strength, and the like. The general daily dose (usual dose) is Formula B (about 7 g) derived from an extract obtained from

*Wisteria floribunda* (2 g), *Myristica fragrans* (2 g), *Punica granatum* (2 g), *Trapa bispinosa* or a derivative thereof (2 g), *Elfvingia applanata* (2 g), *Coix lachryma-jobi* (4 g), *Ganoderma lucidum* or a derivative thereof (4 g) and *Panax ginseng* (or *Panax japonicus*) (4 g).

The present invention is explained in detail by referring to examples. The examples are mere exemplifications and do not limit the present invention in any way.

EXAMPLE 1

Effect of Formula A on Herpes Simplex Virus Type 1

*Wisteria floribunda* (125 g), *Myristica fragrans* (125 g), *Punica granatum* (125 g), *Trapa bispinosa* (125 g), *Elfvingia applanata* (125 g), *Coix lachryma-jobi* (250 g) and *Ganoderma lucidum* (250 g) were weighed. Warm water (11.25 kg) was added to the total amount thereof (1.125 kg), and the mixture was extracted at 90° C.–95° C. for 3 hr. After extraction, the extract was filtrated, and the filtrate (extract) was concentrated under reduced pressure at 50° C. to give starch syrup (weight 260 g). To the concentrate (260 g) was added 520 g of cornstarch and the mixture was kneaded to homogeneity. The kneaded product was dried in a dryer at 60° C.–70° C. for 24 hr. The dry product was pulverized in a mixer to give a powder, whereby a composition having a physiological activity of the present invention was prepared according to the above-mentioned Formula A (hereinafter sometimes to be referred to as Formula A). The usual daily dose was set for 6 g of the above-mentioned Formula A.

The usual dose of Formula A was administered for 3 days to a 62-year-old male who developed herpes labialis due to overwork. As a result, crust was formed at day 3 of the administration and the disease was cured.

EXAMPLE 2

Effect of Formula A on Herpes Simplex Virus Type 1

The Formula A (3-fold amount of usual dose) was administered for 3 days to a 29-year-old female who developed herpes labialis after a cold with high fever. As a result, crust formation began at day 2 of the administration and the disease was completely cured at day 3.

EXAMPLE 3

Effect of Formula A on Herpes Simplex Virus Type 2

The usual dose of Formula A was administered to a 33-year-old female who developed herpes genitalis. As a result, the condition was gradually improved and the patient became asymptomatic in 2 weeks.

EXAMPLE 4

Effect of Formula A on Herpes Simplex Virus Type 2

A half amount of the usual dose of Formula A was administered to a 37-year-old female who was infected with herpes genitalis and diagnosed meningitis herpes 10 days later. The patient continued to take the composition and became almost asymptomatic in 3 weeks.

EXAMPLE 5

Effect of Formula A on Herpes Zoster Virus

The usual dose of Formula A was administered to a 55year-old male who developed herpes zoster on the back of the neck. As a result, the condition was gradually improved and the disease was completely cured in 2 weeks.

EXAMPLE 6

Effect of Formula A on Rubella Virus

The usual dose of Formula A was administered once to a 26-year-old female, who showed slight flare on the neck and face after inoculation of live rubella virus, at 2 days after the inoculation. As a result, the flare disappeared at day 1 of the administration. When the administration was stopped, the flare appeared again.

EXAMPLE 7

Effect of Formula B on Herpes Simplex Virus Type 1

*Wisteria floribunda* (125 g), *Myristica fragrans* (125 g), *Punica granatum* (125 g), *Trapa bispinosa* (125 g), *Elfvingia applanata* (125 g), *Coix lachryma-jobi* (250 g), *Ganoderma lucidum* (250 g) and *Panax ginseng* (Nitto Denko Co., tissue culture *Panax ginseng*, 250 g) were weighed. Warm water (13.75 kg) was added to the total amount thereof (1.375 kg), and the mixture was extracted at 90° C.–95° C. for 3 hr. After extraction, the extract was filtrated, and the filtrate (extract) was concentrated under reduced pressure at 50° C. to give starch syrup (weight 270 g). To the concentrate (270 g) was added 540 g of cornstarch and the mixture was kneaded to homogeneity. The kneaded product was dried in a dryer at 60° C.–70° C. for 24 hr. The dry product was pulverized in a mixer to give a powder, whereby a composition having a physiological activity of the present invention was prepared according to the above-mentioned Formula B (hereinafter sometimes to be referred to as Formula B)). The usual daily dose was set for 6 g of the above-mentioned Formula B.

A half the usual dose of Formula B was administered to a 41-year-old female who developed herpes labialis for initially scheduled period of 14 days. As a result, the condition was improved soon after the start of the administration and completely cured at day 9.

EXAMPLE 8

Effect of Formula B on Herpes Simplex Virus Type 1

The Formula B (3-fold amount of usual dose) was administered for 4 days to a 19-year-old male who developed herpes labialis after a cold with high fever. As a result, crust formation began at day 2 of the administration and the disease was completely cured at day 4.

EXAMPLE 9

Effect of Formula B on Herpes Simplex Virus Type 2

A 34-year-old female, who had been taking the usual dose of Formula B for about one month, was infected with herpes genitalis from her husband, and diagnosed meningitis one week later. However, continuous medication of the usual dose of Formula B resulted in an asymptomatic progress.

EXAMPLE 10

Effect of Formula B on Herpes Zoster Virus

A 2-fold amount of the usual dose of Formula B was administered to a 61-year-old male who developed herpes zoster from the back of the neck to the shoulder due to overwork. As a result, the condition was gradually improved and the disease was completely cured in 20 days.

EXAMPLE 11

Effect of Formula B on Hepatitis B Virus

The usual dose of Formula B was administered to a 39-year-old female who developed hepatitis B from a carrier. At one month from the start of the administration, GOT/GPT temporarily increased, but decreased to a normal level at 11 weeks from the start of the administration. In addition, the patient tested HBe antigen (−) and HBe antibody (+), indicating seroconversion. This means an increased antibody production against virus. After seroconversion, continuous medication for 6 months did not change this state of the patient.

EXAMPLE 12

Effect of Formula A on Peripheral Blood Flow

Formula A was given to 6 adults (30–39 years old, 3 males and 3 females) by 2 g per administration 3 times a day before meal for 14 days, and the total resistance of peripheral blood flow was measured before and after the administration with an automatic sphygmomanometer (Parama-Tech, Co., Ltd., FT-101) capable of measurement of noninvasive hemodynamics based on Korotkoff sounds. The average and standard deviations were determined and comparatively analyzed. As a result, the values obtained was 1670±310 (dyne/sec/cm$^{-5}$) before administration and 1010±270 (dyne/sec/cm$^{-5}$) after administration, showing a significant difference.

EXAMPLE 13

Effect of Formula B on Peripheral Blood Flow

Formula B was given to 6 adults (30–39 years old, 3 males and 3 females) by 2 g per administration 3 times a day before meal for 14 days, and the total resistance of peripheral blood flow was measured before and after the administration with an automatic sphygmomanometer (Parama-Tech, Co., Ltd., FT-101) capable of measurement of noninvasive hemodynamics based on Korotkoff sounds. As a result, the values obtained was 1610±330 (dyne/sec/cm$^{-5}$) before administration and 980±250 (dyne/sec/cm$^{-5}$) after administration, showing a significant difference.

EXAMPLE 14

Effect of Formula A on Alopecia

Formula A was given to a 53-year-old male with alopecia showing hair growth only in a temporal region of the head, by 2 g per administration 3 times a day for 3 months. As a result, hair growth (0.5 cm–1.5 cm) was observed from the hair line of the temporal region of the head. During this period, no side effects were sensed by the test subject.

EXAMPLE 15

Effect of Formula B on Alopecia

Formula B was given to a 39-year-old male with alopecia showing hair growth only in a temporal region of the head, by 2 g per administration 3 times a day for 5 months. As a result, hair growth (0.5 cm–1.5 cm) was observed from the hair line of the temporal region of the head. During this period, no side effects were sensed by the test subject.

EXAMPLE 16

In vitro Antiviral Activity: Formula A Solution and Virus Solution were Mixed and Immediately Added to Culture Cell The virus used was herpes simplex virus type 2 (UW268 strain) and the cell used was MA104 cell (rhesus monkey kidney derived cell). Formula A was dissolved in Eagle's MEM without FBS at 0.1 g/100 ml, to which solution (0.9 ml) was added virus solution (0.1 ml). The $10^1$–$10^8$ dilute solutions were immediately prepared, and each dilute solution (0.025 ml) was added to culture cells in a 96 well plate. For control, a dilute solution without Formula A was added in the same manner. The cells were cultured at 35° C. for 1 week and a cytopathogenic effect of the virus was observed. The dilution rate of the virus solution, in which virus infection was observed in 50% of the culture cells, was stochastically calculated and virus infection titer (TCID$_{50}$/ml) was determined, according to a Reed-Munch method. As a result, addition of Formula A showed TCID$_{50}$=$10^{4.2}$ in contrast to TCID$_{50}$=$10^{7.2}$ of the control, showing the antiviral activity.

EXAMPLE 17

In vitro Antiviral Activity: Addition of Formula A Solution After Addition of Virus to Culture Cells A $10^1$–$10^8$ dilute virus solution (0.025 ml) was added to culture cells in a 96 well plate. The cells remained at room temperature for 3 hr. Then, a Formula A solution diluted to 0.1 g/100 ml with Eagle's MEM without FBS was added to culture cells in a 96 well plate by 0.025 ml. For control, a solution without Formula A was added in the same manner. The cells were cultured at 35° C. for 1 week and a cytopathogenic effect of the virus was observed. The virus infection titer (TCID$_{50}$/ml) was determined according to a Reed-Munch method. As a result, addition of Formula A showed TCID$_{50}$=$10^{4.6}$ in contrast to TCID$_{50}$=$10^{7.0}$ of the control, showing the antiviral activity.

EXAMPLE 18

Effect of Formula B on Natural Killer Cell Activity

A ⅓-fold amount of the usual dose of Formula B was administered to 5 healthy women for 90 days. The blood was drawn before the administration, and 1, 2 and 3 months after the administration, and the natural killer cell activity in blood was examined. The results are shown in FIG. 1. The natural killer cell activity increased after administration in comparison to that before the administration.

Comparative Example 1

The test subject (62 years old, male) in Example 1 got relapse of herpes labialis. The usual dose of Formula A without the *Wisteria floribunda* component was administered to the test subject for 3 days. As a result, herpes labialis disease state was not improved at all even at day 3 of the administration.

INDUSTRIAL APPLICABILITY

The composition of the present invention has a superior antiviral activity, peripheral blood flow-improving activity and hair growth-stimulating activity, and is useful as a pharmaceutical composition.

The composition of the present invention as an agent for treating virus infections has a superior antiviral activity and is useful for the prophylaxis, treatment, alleviation of symptoms or prevention of aggravation of conditions in infectious diseases caused by various viruses such as viruses of the herpes family (e.g., herpes simplex virus type 1 and type 2, varicella-zoster virus and the like), rubella virus, hepatitis B virus and the like, prophylaxis of diseases caused by virus sustained inductive cancer and the like.

Moreover, the composition of the present invention as a peripheral blood flow-improving agent is effective in that it decreases total peripheral resistance to promote improvement in the blood flow and enhances healing power. The peripheral blood flow-improving agent is useful for the treatment or prophylaxis of arteriosclerosis, Raynaud's disease, Burger's disease and the like.

Furthermore, the composition of the present invention as a hair growth stimulant is useful in that it promotes hair growth in alopecia without side effects caused by the administration.

This application is based on application No. 2001-223334 filed in Japan, the contents of which are incorporated hereinto by reference.

What is claimed is:

1. A composition containing for treating a viral infectious disease caused by herpes virus, consisting essentially of an extract from (a) *Wisteria floribunda*, (b) *Myristica fragrans*, (c) *Punica granatum*, (d) *Trapa bispinosa, Trapa natans, Trapa bicornus*, or *Trapa Japonica*, (e) *Coix lachryma-jobi*, (f) *Elfvingia applanata* and (g) *Ganoderma lucidum* or *Ganoderma japonicum*.

2. The composition of claim 1, wherein the extract is a hot water extract.

3. The composition of claim 1, which consists essentially of an extract obtained from 0.5 part by weight-5 parts by weight of *Myristica fragrans*, 0.5 part by weight-5 parts by weight of *Punica granatum*, 0.5 part by weight-5 parts by weight of *Trapa bispinosa, Trapa natans, Trapa bicornus*, or *Trapa japonica*, 0.5 part by weight-5 parts by weight of *Elfvingia applanata*, 0.5 part by weight-5 parts by weight of *Coix lachryma-jobi*, and 0.5 part by weight-5 parts by weight of *Ganoderma lucidum* or *Ganoderma japonicum*, per 1 part by weight of *Wisteria floribunda*.

4. The composition of claim 3, which consists essentially of an extract obtained from 1 part by weight of *Myristica fragrans*, 1 part by weight of *Punica granatum*, 1 part by weight of *Trapa bispinosa, Trapa natans, Trapa bicornus*, or *Trapa japonica*, 1 part by weight of *Elfvingia applanata*, 2 parts by weight of *Coix lachryma-jobi*, and 2 parts by weight-3 parts by weight of *Ganoderma lucidum* or *Ganoderma japonicum*, per 1 part by weight of *Wisteria floribunda*.

5. The composition of claim 4, which consists essentially of an extract obtained from 1 part by weight of *Myristica fragrans*, 1 part by weight of *Punica granatum*, 1 part by weight of *Trapa bispinosa, Trapa natans, Trapa bicornus*, or *Trapa japonica*, 1 part by weight of *Elfvingia applanata*, 2 parts by weight of *Coix lachryma-jobi* and 2 parts by weight of *Ganoderma lucidum* or *Ganoderma japonicum*, per 1 part by weight of *Wisteria floribunda*.

6. The composition of claim 1, wherein the herpes virus is a herpes simplex virus or a varicella-zoster virus.

7. A composition containing for treating a viral infectious diease caused by herpes virus, consisting essentially of an extract from (a) *Wisteria floribunda*, (b) *Myristica fragrans*, (c) *Punica granatum*, (d) *Trapa bispinosa, Trapa natans, Trapa bicornus*, or *Trapa Japonica*, (e) *Coix lachryma-jobi*, (f) *Elfvingia applanata* and (g) *Ganoderma lucidum* or *Ganoderma japonicum*, and (h) *Panax ginseng* and *Panax japonicus*.

8. The composition of claim 7, wherein the extract is a hot water extract.

9. The composition of claim 7, which consists essentially of an extract obtained from 0.5 part by weight-5 parts by weight of *Myristica fragrans*, 0.5 part by weight-5 parts by weight of *Punica granatum*, 0.5 part by weight-5 parts by weight of *Trapa bispinosa, Trapa natans, Trapa bicornus*, or *Trapa japonica*, 0.5 part by weight-5 parts by weight of *Elfvingia applanata*, 0.5 part by weight-5 parts by weight of *Coix lachryma-jobi*, 0.5 part by weight-5 parts by weight of *Ganoderma lucidum* or *Ganoderma japonicum*, and 0.5 part by weight-5 parts by weight of *Panax ginseng* or *Panax japonicus*, per 1 part by weight of *Wisteria floribunda*.

10. The composition of claim 9, which consists essentially of an extract obtained from 1 part by weight of *Myristica fragrans*, 1 part by weight of *Punica granatum*, 1 part by weight of *Trapa bispinosa, Trapa natans, Trapa bicornus*, or *Trapa japonica*, 1 part by weight of *Elfvingia applanata*, 2 parts by weight of *Coix lachryma-jobi*, 2 parts by weight-3 parts by weight of *Ganoderma lucidum* or *Ganoderma japonicum*, and 0.5 part by weight-3 parts by weight of *Panax ginseng* or Panax japonicus, per 1 part by weight of *Wisteria floribunda*.

11. The composition of claim 10, which consists essentially of an extract obtained from 1 part by weight of *Myristica fragrans*, 1 part by weight of *Punica granatum*, 1 part by weight of *Trapa bispinosa, Trapa natans, Trapa bicornus*, or *Trapa japonica*, 1 part by weight of *Elfvingia applanata*, 2 parts by weight of *Coix lachryma-jobi*, 2 parts by weight of *Ganoderma lucidum* or *Ganoderma japonicum*, and 2 parts by weight of *Panax ginseng* or *Panax japonicus*, per 1 part by weight of *Wisteria floribunda*.

12. A method for producing a composition for treating a viral infectious disease caused by herpes virus, which method consists essentially of extracting (a) *Wisteria floribunda*, (b) *Myristica fragrans*, (c) *Punica granatum*, (d) *Trapa bispinosa, Trapa natans, Trapa bicornus*, or *Trapa japonica*, (e) *Coix lachryma-jobi*, (f) *Elfvingia applanata*, and (g) *Ganoderma lucidum* or *Ganoderma japonicum*, with hot water.

13. The production method of claim 12, which method consists essentially of extracting, with hot water, 0.5 part by weight-5 parts by weight of *Myristica fragrans*, 0.5 part by weight-5 parts by weight of *Punica granatum*, 0.5 part by weight-5 parts by weight of *Trapa bispinosa, Trapa natans, Trapa bicornus*, or *Trapa japonica*, 0.5 part by weight-5 parts by weight of *Elfvingia applanata*, 0.5 part by weight-5 parts by weight of *Coix lachryma-jobi*, and 0.5 part by weight-5 parts by weight of *Ganoderma lucidum* or *Ganodermajaponicum*, per 1 part by weight of *Wisteria floribunda*.

14. The production method of claim 12, wherein the hot water extraction is performed at 80° C.–100° C. for not less than 1 hr.

15. The production method of claim 14, wherein the hot water extraction is performed at 90° C.–95° C. for not less than 1 hr.

16. A method for producing a composition for treating a viral infectious disease caused by herpes virus, which method consists essentially of extracting (a) *Wisteria floribunda*, (b) *Myristica fragrans*, (c) *Punica granatum*, (d) *Trapa bispinosa, Trapa natans, Trapa bicornus*, or *Trapa japonica*, (e) *Coix lachryma-jobi*, (f) *Efvingia applanata*, (g) *Ganoderma lucidum* or *Ganoderma japonicum*, and (h) *Panax ginseng* or *Panax japonicus* with hot water.

17. The production method of claim 16, which method consists essentially of extracting, with hot water, 0.5 part by weight-5 parts by weight of *Myristica fragrans,* 0.5 part by weight-5 parts by weight of *Punica granatum,* 0.5 part by weight-5 parts by weight of *Trapa bispinosa, Trapa natans, Trapa bicornus,* or *Trapa japonica,* 0.5 part by weight-5 parts by weight of *Elfvingia applanata,* 0.5 part by weight-5 parts by weight of *Coix lachryma-jobi,* 0.5 part by weight-5 parts by weight of *Ganoderma lucidum* or *Ganoderma japonicum,* and 0.5 part by weight-5 parts by weight of *Panax ginseng* or *Panax japonicus,* per 1 part by weight of *Wisteria floribunda.*

* * * * *

UNITED STATES PATENT AND TRADEMARK OFFICE
CERTIFICATE OF CORRECTION

PATENT NO.    : 6,953,580 B2
DATED         : October 11, 2005
INVENTOR(S)   : Tanaka et al.

It is certified that error appears in the above-identified patent and that said Letters Patent is hereby corrected as shown below:

Column 13,
Line 22, "composition containing for" should read -- composition for --.
Lines 26 and 64, "*Trapa Japonica*" should read -- *Trapa japonica* --.
Lines 27 and 65, "*Elfvingia applanata* and" should read -- *Elfvingia applanata*, and --.
Line 60, "composition containing for" should read -- composition for --.
Line 66, "*Panax ginseng* and" should read -- *Panax ginseng* or --.

Column 14,
Line 22, "Panax japonicus" should read -- *Panax japonicus* --.
Line 50, "*Ganodermajaponicum*" should read -- *Ganoderma japonicum* --.

Signed and Sealed this

Twenty-eighth Day of February, 2006

JON W. DUDAS
*Director of the United States Patent and Trademark Office*